(12) United States Patent
Glazer et al.

(10) Patent No.: US 8,951,293 B2
(45) Date of Patent: Feb. 10, 2015

(54) ORTHOPEDIC SCREW INSERT

(75) Inventors: Paul Andrew Glazer, Chestnut Hill, MA (US); Robert Jordan, Malden, MA (US); John Haroutunian, Danvers, MA (US)

(73) Assignee: NuVasive, Inc., San Diego, CA (US)

( * ) Notice: Subject to any disclaimer, the term of this patent is extended or adjusted under 35 U.S.C. 154(b) by 154 days.

(21) Appl. No.: 13/524,968

(22) Filed: Jun. 15, 2012

(65) Prior Publication Data
US 2012/0259372 A1 Oct. 11, 2012

Related U.S. Application Data

(63) Continuation of application No. 12/009,441, filed on Jan. 18, 2008, now Pat. No. 8,221,479.

(60) Provisional application No. 60/881,110, filed on Jan. 19, 2007.

(51) Int. Cl.
| | |
|---|---|
| *A61B 17/04* | (2006.01) |
| *A61B 17/86* | (2006.01) |
| *A61F 2/08* | (2006.01) |
| *A61B 17/84* | (2006.01) |
| *F16B 13/06* | (2006.01) |
| *A61B 17/68* | (2006.01) |

(52) U.S. Cl.
CPC .................................. *A61B 17/686* (2013.01)
USPC ............... 606/303; 606/326; 411/58; 411/63; 411/60.2

(58) Field of Classification Search
CPC ..................................................... A61B 17/686
USPC ..................... 606/303, 326; 411/58, 60.2, 63
See application file for complete search history.

(56) References Cited

U.S. PATENT DOCUMENTS

| | | | | |
|---|---|---|---|---|
| 1,755,264 | A * | 4/1930 | Mirzan | 411/60.2 |
| 3,298,725 | A * | 1/1967 | Boteler | 403/282 |
| 3,516,324 | A * | 6/1970 | Berner | 411/72 |
| 3,896,504 | A | 7/1975 | Fischer | |
| 4,611,581 | A | 9/1986 | Steffee | |
| 4,614,471 | A * | 9/1986 | Mauritz | 411/21 |
| 4,711,232 | A * | 12/1987 | Fischer et al. | 606/67 |
| 4,716,893 | A * | 1/1988 | Fischer et al. | 606/66 |
| 4,760,843 | A * | 8/1988 | Fischer et al. | 606/304 |
| 4,805,260 | A * | 2/1989 | Tooth | 16/37 |
| 5,004,421 | A | 4/1991 | Lazarof | |
| 5,065,490 | A * | 11/1991 | Wivagg et al. | 29/402.17 |
| 5,209,753 | A * | 5/1993 | Biedermann et al. | 606/304 |
| 5,303,718 | A * | 4/1994 | Krajicek | 128/897 |
| 5,489,210 | A | 2/1996 | Hanosh | |
| 5,520,690 | A | 5/1996 | Errico et al. | |

(Continued)

*Primary Examiner* — David Bates
(74) *Attorney, Agent, or Firm* — Jonathan Spangler; Rory Schermerhorn (57) ABSTRACT

An insert for receiving a bone screw includes an elongate sleeve having opposed proximal and distal ends and a wall defined by an outer peripheral surface configured for engaging bone and an inner peripheral surface configured for receiving a bone screw extended therethrough. At least one elongate slot is formed in the wall of the sleeve for promoting flexure of the insert. A tool for affixing an orthopedic screw insert within bone tissue includes a socket portion configured and adapted to engage a proximal section of an outer peripheral surface of an orthopedic screw insert. A driver extends distally from the socket portion. The driver is configured and adapted to engage a section of an inner peripheral surface of the orthopedic screw insert distal from the socket portion.

15 Claims, 4 Drawing Sheets

(56) References Cited

U.S. PATENT DOCUMENTS

| | | |
|---|---|---|
| 5,531,746 A | 7/1996 | Errico et al. |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,643,265 A | 7/1997 | Errico et al. |
| 5,647,873 A | 7/1997 | Errico et al. |
| 5,667,507 A | 9/1997 | Corin et al. |
| 5,669,911 A | 9/1997 | Errico et al. |
| 5,690,630 A | 11/1997 | Errico et al. |
| 5,713,904 A * | 2/1998 | Errico et al. .................. 606/327 |
| 5,725,528 A | 3/1998 | Errico et al. |
| 5,725,581 A * | 3/1998 | Brånemark .................. 606/304 |
| 5,725,588 A | 3/1998 | Errico et al. |
| 5,735,851 A | 4/1998 | Errico et al. |
| 5,776,135 A | 7/1998 | Errico et al. |
| 5,785,711 A | 7/1998 | Errico et al. |
| 5,810,819 A | 9/1998 | Errico et al. |
| 5,817,094 A | 10/1998 | Errico et al. |
| 5,899,904 A | 5/1999 | Errico et al. |
| 5,899,905 A | 5/1999 | Errico et al. |
| 5,925,047 A | 7/1999 | Errico et al. |
| 5,947,969 A | 9/1999 | Errico et al. |
| 5,961,518 A | 10/1999 | Errico et al. |
| 5,997,539 A | 12/1999 | Errico et al. |
| 6,017,344 A | 1/2000 | Errico et al. |
| 6,063,089 A | 5/2000 | Errico et al. |
| 6,276,882 B1 * | 8/2001 | Young .......................... 411/60.2 |
| 6,293,743 B1 | 9/2001 | Ernst et al. |
| 6,482,207 B1 | 11/2002 | Errico |
| RE39,089 E | 5/2006 | Ralph et al. |
| 8,128,670 B2 * | 3/2012 | Ralph et al. .................... 606/313 |
| 8,162,998 B2 * | 4/2012 | Schlienger et al. ........... 606/315 |
| 2002/0147454 A1 * | 10/2002 | Neto .............................. 606/73 |
| 2005/0177161 A1 | 8/2005 | Baynham et al. |
| 2006/0106390 A1 * | 5/2006 | Jensen et al. ..................... 606/73 |
| 2008/0039846 A1 * | 2/2008 | Lee et al. ......................... 606/63 |

* cited by examiner

ORTHOPEDIC SCREW INSERT

CROSS-REFERENCE TO RELATED APPLICATION

This application is a continuation application of U.S. patent application Ser. No. 12/009,441 filed Jan. 18, 2008 which claims the benefit of priority from U.S. Provisional Patent Application Ser. No. 60/881,110, filed Jan. 19, 2007, each of which is incorporated by reference herein in its entirety.

BACKGROUND OF THE INVENTION

1. Field of the Invention

The present invention relates to a screw insert, and more particularly, to an insert for receiving a bone screw to increase the anchoring strength of the bone screw.

2. Description of Related Art

A variety of devices are known in the art for anchoring surgical components to bones. Of such devices, many are directed to bone screws for attaching bones together or to attaching prostheses to bones. There are several uses for bone screws in treating spinal conditions, treating joints, and anchoring sutures to bones, among others.

Typically, when a bone screw is implemented to treat a bone condition, a drill is used to bore into the bone. The resulting bore typically extends through cortical bone and into cancellous bone. After the bore is formed, a bone screw can be driven into the bore with the threads engaging the bone where possible. Various items can then be anchored to the bone by means of the bone screw in place within the bore.

The anchoring strength of bone screws as described above is limited. Anchoring strength can be limited by defects in the bone. For example, osteoporotic bone in older patients is much weaker than bone in young, healthy patients. Errors in the placement of the bore can also compromise the anchoring strength of bone screws. For example, current orthopedic devices used in the spine rely on screws inserted directly into the vertebral structure. Fixation strength is highly dependent not only on strength and integrity of the bone, but also on the placement of the bores. This is a significant limitation for spinal devices, especially those aimed at non-fusion applications such as dynamic stabilization devices. Placement and insertion of bores and screws is often difficult in bony structures such as the pedicle or facet. An alignment mistake can lead to the bore lying too close to or breaking through the cortex on one side of the bone structure. When a bone is compromised in this manner, it may provide inadequate load distribution for use of a conventional bone screw.

Conventional methods and systems of anchoring structures to bones generally have been considered satisfactory for their intended purpose. However, there remains an ever present need to advance the state of the art for increasing the anchoring strength of structures like bone screws. There also remains a need in the art for a method and a system that can increase the anchoring strength of bone screws in defective bone tissue or compromised bores. The present invention provides a solution for these problems.

SUMMARY OF THE INVENTION

The subject invention is directed to a new and useful insert for receiving a bone screw. The insert includes an elongate sleeve having opposed proximal and distal ends. A wall of the sleeve is defined by an outer peripheral surface configured for engaging bone and an inner peripheral surface configured for receiving a bone screw extended therethrough. At least one elongate slot is formed in the wall of the sleeve for promoting flexure of the insert. In one embodiment, the sleeve includes at least one distal elongate slot extending from the distal end of the sleeve and at least one proximal elongate slot extending from the proximal end of the sleeve.

The elongate sleeve has a middle region between the proximal and distal ends thereof. The at least one distal slot can extend from the distal end through the middle region of the sleeve toward the proximal end, and the at least one proximal slot can extend from the proximal end of the sleeve through the middle region toward the distal end. The lengths of the proximal and distal slots in this configuration thus overlap each other in the middle region of the sleeve. It is contemplated that the middle region of the sleeve can extend over at least 20% of the length of the sleeve, about 40% of the length of the sleeve, or any other suitable fraction of the length of the sleeve. It is also possible for circumferentially alternating slots to be distal slots in the middle region of the sleeve. In one embodiment, the insert has a plurality of elongate slots that includes at least one pair of diametrically opposed distal slots extending from the distal end of the sleeve and at least one pair of diametrically opposed proximal slots extending from the proximal end of the sleeve.

In another embodiment, the sleeve includes four distal slots and four proximal slots. The four distal slots can extend between about 60% and about 75% of the length of the insert. It is also possible for the four distal slots to extend along any suitable portion of the length of the insert. The four proximal slots can be the same length as the four distal slots. It is also possible for the four proximal slots to be dimensioned to extend a shorter length than the distal slots, overlapping the distal slots and extending more than half the length of the insert. Moreover, any suitable slot lengths or configurations can be used.

It is contemplated that the inner peripheral surface of the sleeve can be configured and adapted to threadably engage with threads of a bone screw. The inner peripheral surface of the sleeve can be configured and adapted to engage a bone screw to expand at least a portion of the sleeve when the sleeve receives a bone screw. A distal section of the inner peripheral surface of the sleeve can be configured and adapted to expand against threads of a bone screw received in the sleeve so a distal section of the outer peripheral surface engages with cancellous bone. It is also contemplated that a proximal section of the inner peripheral surface of the sleeve can be configured and adapted to expand against a bone screw received in the sleeve so a proximal section of the outer peripheral surface engages with cortical bone. The inner peripheral surface can be configured and adapted to engage a bone screw to expand both distal and proximal end portions of the sleeve when the sleeve receives a bone screw.

The outer peripheral surface of the sleeve can include a sharpened helical cutting edge along at least a portion thereof, the sharpened edge being configured and adapted to increase fixation strength when the insert engages bone tissue through self-tapping. The insert can further include a head portion at a proximal end of the sleeve, wherein the head portion is configured and adapted to engage a tool for driving the sleeve into a bone. The head portion can include a polygonal outer peripheral surface configured and adapted to engage a tool for driving the sleeve into a bone. It is contemplated that the polygonal outer peripheral surface can be hexagonal, octagonal, or any other suitable shape.

The sleeve can include a biocompatible material selected from the group consisting of titanium alloys, plastics, composites, stainless steel, or any other suitable material. A polymer coating can be disposed on at least a portion of the sleeve to provide resistance to turning of a bone screw when engaged within the insert. It is also contemplated that plasma treatment, hydroxyapatite coatings, bead blasting, or any other suitable surface treatments can be used to promote fixation of the insert in bone.

The insert can be used to increase anchoring strength of orthopedic screws in a variety of different applications, including treatment of broken bones, anchoring sutures, total joint replacements, acetabular cups, replacement hips, iliac procedures, anterior vertebral body fixation, pedicle fixation, facet fixation, dynamic stabilization devices, and any other suitable application. It is also possible to use the insert to repair failed fixations of traditional bone screws. The insert length, diameter, internal and external surface contours, and other configuration variables can be of any suitable combination for use from application to application.

A tool is also provided for affixing an orthopedic screw insert within bone tissue. The tool includes a socket portion configured and adapted to engage a proximal section of an outer peripheral surface of an orthopedic screw insert. A driver extends distally from the socket portion. The driver is configured and adapted to engage a section of an inner peripheral surface of the orthopedic screw insert distal from the socket portion.

In one embodiment of the tool, the socket portion includes a polygonal section configured and adapted to engage a polygonal head portion of the outer peripheral surface of the orthopedic screw insert. The polygonal section can be hexagonal, octagonal, or any other suitable shape. It is also contemplated that the driver can include a plurality of radially extending fins configured and adapted to engage a corresponding plurality of slots in the inner peripheral surface of the orthopedic screw insert.

A method is also provided for securing an orthopedic screw in bone tissue. The method includes identifying a target site for an orthopedic screw in a bone and forming a bore in the bone at the target site. An insert is driven into the bore with a tool that supports the insert from within the insert. The tool is removed from the insert, and an orthopedic screw is driven into the insert to securely mount the orthopedic screw to the bone. The method can optionally include tapping the bore for threadable engagement with the insert. Moreover, the step of driving can include driving a distal portion of the insert with a plurality of fins extending radially outward from the tool within the insert for engaging a plurality of slots defined in the insert.

These and other features and benefits of the insert of the subject invention and the manner of anchoring a bone screw in a bone will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the insert and method of anchoring a bone screw according to the subject invention without undue experimentation, preferred embodiments thereof will be described in detail hereinbelow with reference to certain figures, wherein.

DETAILED DESCRIPTION OF THE PREFERRED EMBODIMENT

Figure 1:
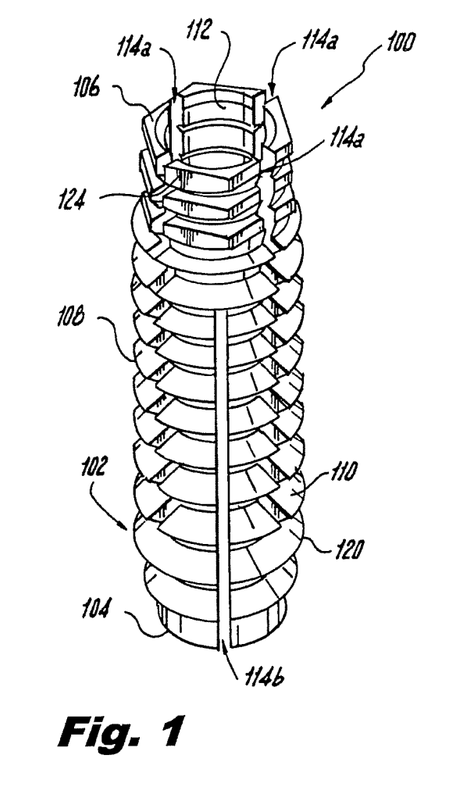
FIG. 1 is a perspective view of a representative embodiment of an insert for receiving a bone screw in accordance with the present invention, showing elongate slots in the wall of the insert.

Referring now to the drawings, wherein like reference numerals identify or otherwise refer to similar structural features or elements of the various embodiments of the subject invention, there is illustrated in FIG. 1 an insert for receiving a bone screw designated generally by reference character 100.

Figure 2:
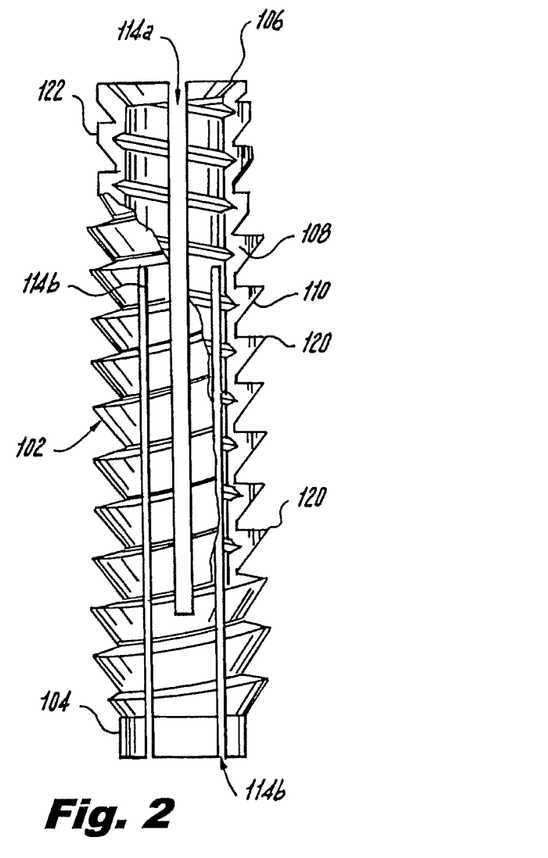
FIG. 2 is a partially cross-sectional side elevation view of the insert of FIG. 1 in accordance with the present invention, showing the threaded portions of the inner peripheral surface of the insert.

As depicted in FIGS. 1 and 2, insert 100 includes a sleeve 102 with a distal end 104 and a proximal end 106. A wall 108 of sleeve 102 is defined between outer peripheral surface 110 and inner peripheral surface 112. Elongate slots 114*a*, 114*b* are defined through the thickness of wall 108 from outer peripheral surface 110 to inner peripheral surface 112.

Slot 114*a* is a proximal slot extending from proximal end 106 of sleeve 102, through a middle portion of the sleeve, and ending proximal from distal end 104 of sleeve 102. Slot 114*b*, on the other hand, is a distal slot that extends from distal end 104, through a middle portion of the sleeve, and ends short of proximal end 106 of sleeve 102. Thus, while proximal slot 114*a* and distal slot 114*b* extend from opposite ends of sleeve 102, portions of their respective lengths overlap, or are coextensive with each other, in the middle portion of sleeve 102.

The middle portion of sleeve 102 where proximal and distal slots 114a, 114b overlap represents approximately 40% of the length of sleeve 102. However, this length can be 20%, 50%, 60%, or any other fraction of the length of sleeve 102 that lends suitable flexibility. Moreover, while the middle portion of sleeve 102 as depicted includes the center of the length of sleeve 102, it is not necessary for the middle portion to be centered on sleeve 102. It is possible for the middle portion to be located anywhere between the proximal and distal end of sleeve 102.

Figure 3:
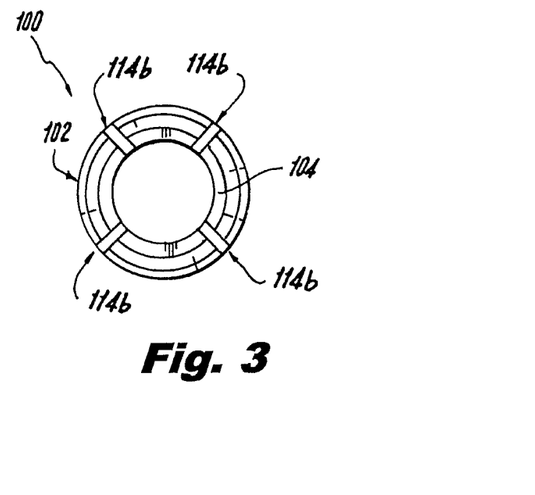
FIG. 3 is a distal end view of the insert of FIG. 1 in accordance with the present invention, showing the distal slots extending from the distal end of the insert.
Figure 4:
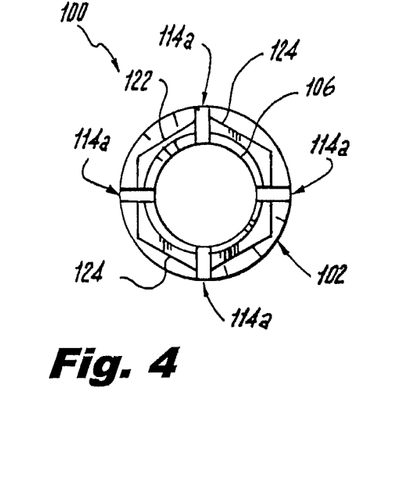
FIG. 4 is a proximal end view of the insert of FIG. 1 in accordance with the present invention, showing the proximal slots extending from the proximal end of the insert, as well as the hexagonal head portion of the insert.

As shown in FIG. 3, sleeve 102 includes two pairs of diametrically opposed distal slots 114b. FIG. 4 shows that sleeve 100 also includes two pairs of diametrically opposed proximal slots 114a. The four distal slots 114b are about 60%-75% as long as the insert. The four proximal slits 114a extend over half way to distal end 104 of sleeve 102 and are of roughly the same length as distal slots 114b. However, those skilled in the art will readily appreciate that it is not necessary for proximal and distal slots 114a, 114b to overlap. Each slot 114a, 114b may be of a different length. Moreover, any suitable lengths for insert 100 and slots 114a, 114b for promoting flexure can be used without departing from the spirit and scope of the invention.

As shown in FIGS. 3 and 4, sleeve 102 includes proximal slots 114a and distal slots 114b spaced substantially 45° apart in an alternating pattern around the circumference of sleeve 102. This configuration of proximal and distal slots 114a, 114b makes sleeve 102 flexible along substantially its entire length, allowing expansion near distal end 104 and proximal end 106. It is possible for insert 100 to include one slot that extends all the way from proximal end 106 to distal end 104 of sleeve 102. It is also possible for sleeve 102 to have slots extending from only one end. Thus, while insert 100 is described herein as having eight slots 114a, 114b, four being proximal slots 114a that alternate with four distal slots 114b, those skilled in the art will readily appreciate that any suitable number of slots and slot configurations can be used. Moreover, while slots 114a and 114b are shown as being substantially straight lines parallel with the length of insert 100, it is also possible to use slots that are spiraled, angled, curved, or of any other suitable configuration without departing from the spirit and scope of the invention.

Figure 5:
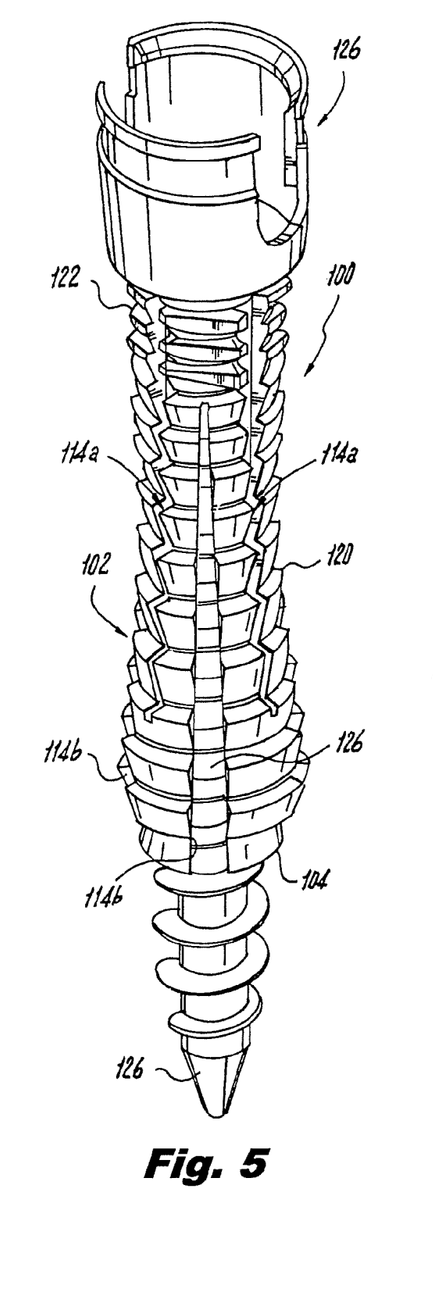
FIG. 5 is a perspective view of the insert of FIG. 1 in accordance with the present invention, showing the insert with an orthopedic screw extending therethrough, expanding the proximal and distal end portions of the insert.

FIG. 5 shows insert 100 with an orthopedic screw passing therethrough. Slots 114a, 114b provide flexibility for insert 100 to accommodate the screw while expanding outward. While the entire length of insert 100 can be generally expanded with the screw in place, it is advantageous in some applications for proximal end 106 and/or distal end 104 to be expanded to a greater extent than the middle portion of insert 100, as will be described below.

Referring again to FIGS. 1 and 2, wall 108 of sleeve 102 is defined between outer peripheral surface 110 and inner peripheral surface 112. Inner peripheral surface 112 is configured to receive an orthopedic screw therethrough. Outer peripheral surface 110 is configured and adapted to engage bone tissue to provide increased anchoring strength to an orthopedic screw extending through sleeve 102.

Inner peripheral surface 112 has internal threads for threadable engagement with the threads of an orthopedic screw, as depicted in FIG. 5. The threaded portion of inner surface 112 has a diameter dimensioned to fit the threads of a respective orthopedic screw with a non-interference fit, however it is also possible to configure inner surface 112 for an interference fit. A wide variety of thread configurations exist for orthopedic screws, which tend to vary from manufacture to manufacturer. Those skilled in the art will readily appreciate how to configure the internal threads to conform to the thread pattern of a particular screw.

Figure 6:
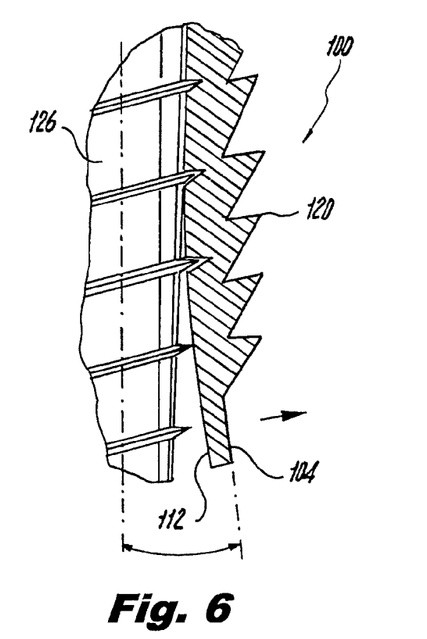
FIG. 6 is a partial cross-sectional side elevation view of a portion of the insert of FIG. 1 in accordance with the present invention, showing the threads of the orthopedic screw pressing outward on the distal end of the insert.

As shown in FIG. 6, in order to cause distal end 104 to expand when an orthopedic screw 126 is in place, a distal portion of inner peripheral surface 112 is not threaded. Thus when the orthopedic screw is driven into insert 100, as the threads meet the thread-free portion of inner surface 112, the threads of the screw press outward against the thread free portion, which must expand outward to accommodate the screw, as shown by arrows in FIG. 6. As shown in FIG. 5, orthopedic screw 126 has an enlarged proximal end that can be driven into proximal end 106 of sleeve 100 to expand proximal end 106.

It is possible to vary the features of inner surface 112 in other ways to expand different portions of insert 100 when used with orthopedic screws in different applications, including use of inward protrusions or other contours tailored to create a specific expansion pattern. Those skilled in the art will readily appreciate that the contours of inner peripheral surface 112 and/or its threads can be configured and adapted to provide various different expansion patterns suitable for different applications.

Referring again to FIG. 2, outer peripheral surface 110 of insert 100 includes a sharpened cutting edge 120 configured to increase fixation strength when insert 100 fixes an orthopedic screw in bone tissue. Cutting edge 120 is depicted as being a helical edge, interrupted by slots 114a, 114b, winding along most of the length of insert 100. Cutting edge 120 provides the advantage of being able to perform self-tapping a bore in bone tissue if necessary. The helical configuration of cutting edge 120 assists in driving insert 100 deeper into bone tissue, however it is not necessary for cutting edge 120 to be helical. Moreover, it is not necessary to have a helical cutting edge, indeed any outer peripheral surface configuration suitable for increasing fixation strength of insert 100 in a bone can be used without departing from the spirit and scope of the invention.

Referring again to FIG. 1, a head portion 122 of outer surface 110 adjacent proximal end 106 of insert 100 is faceted to form a polygonal surface 124. Polygonal surface 124 can be formed by removing portions of cutting edge 120 to form facets along the first few threads adjacent to proximal end 106. As shown in FIG. 4, polygonal surface 124 is hexagonal for convenient engagement with a tool, such as a socket or wrench for driving insert 100 into a bore in a bone. However, it is also contemplated that polygonal surface 120 can be octagonal or any other suitable shape.

Figure 7:
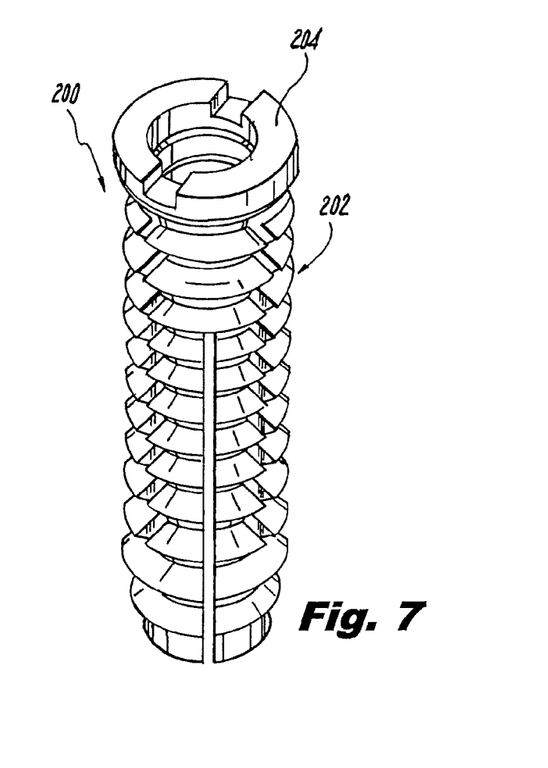
FIG. 7 is a perspective view of a second embodiment of an insert for receiving a bone screw in accordance with the invention, showing a slotted head portion on the proximal end of the insert.

FIG. 7 shows another embodiment of an insert 200 in accordance with the invention. Insert 200 includes sleeve 202 that is similar to sleeve 102 described above. Insert 200 also includes a head sleeve 204, with a central bore therethrough for accommodating an orthopedic coil screw passing into sleeve 202. Head sleeve 204 is slotted across its proximal end to engage a screw driver-type tool for driving insert 200 into a bore in bone tissue. Those skilled in the art will readily appreciate that any other suitable type of head portion can be used without departing from the spirit and scope of the invention.

Insert 100 can be made from biocompatible materials including titanium alloys, plastics, composites, stainless steel, or any other suitable material. It is also possible to include a coating of polymer materials, proteinaceous materials, biologic materials, or any other suitable coating materials on the inner peripheral surface 112 to reduce or prevent turning of an orthopedic screw once in place within insert 100, or on outer peripheral surface 110 to facilitate fixation, or in other configurations to facilitate use of insert 100. Those skilled in the art will appreciate that other surface treatments can be used to promote fixation of the insert in bone, including plasma treatment, hydroxyapatite coatings, bead blasting, or any other suitable surface treatment.

Figure 8:
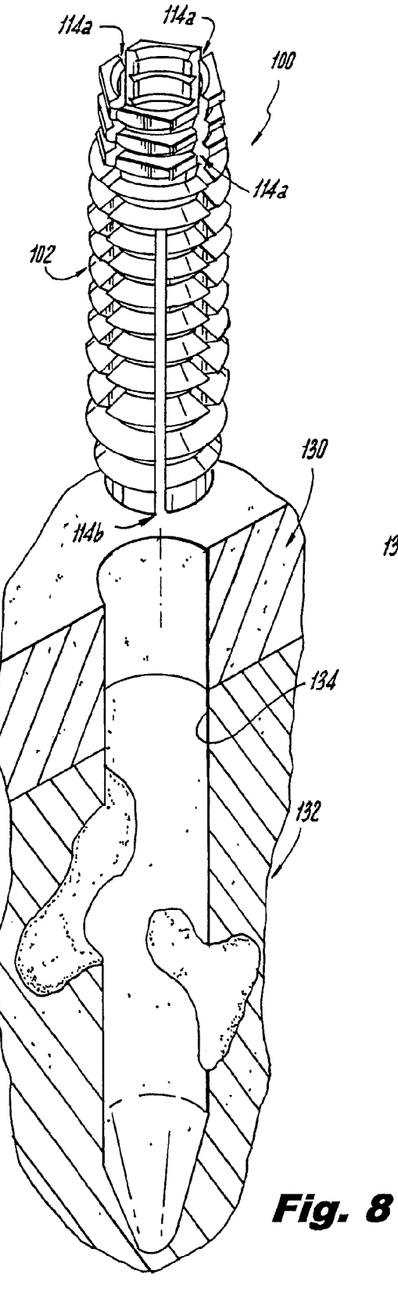
FIG. 8 is a perspective view of the insert of FIG. 1 in accordance with the present invention, showing the insert outside of a bore extending through the cortex and into the cancellous portion of a bone.

FIG. 8 shows a typical bore 134 that has been drilled out of bone tissue for implanting an orthopedic screw. Bore 134 extends through cortical bone tissue 130 into cancellous bone tissue 132. Cancellous bone 132 is softer than cortical bone 130 and is porous. As a result, typical orthopedic screws used alone do not gain the same amount of purchase in cancellous bone 132 as in cortical bone 130. This is especially acute in osteoporotic bone tissue.

Figure 9:
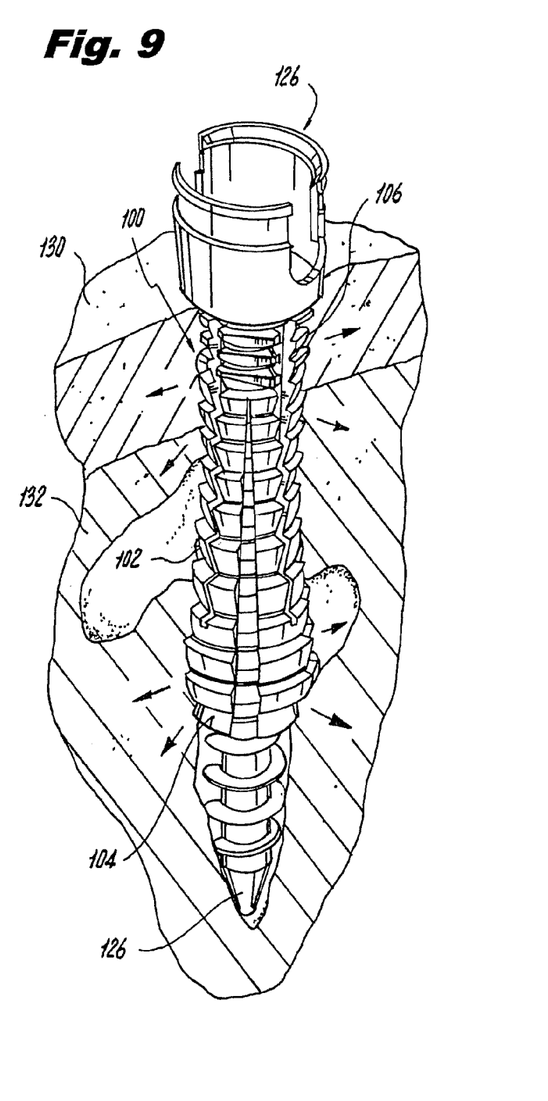
FIG. 9 is a perspective view of the insert of FIG. 1 in accordance with the present invention, showing the insert and orthopedic screw implanted within the bore of FIG. 8.

To increase the anchoring strength of orthopedic screw 126 in bore 124, insert 100 is first driven into bore 124 with a suitable tool. If bore 134 is not pre-threaded, insert 100 can self-tap its way into bore 134 by means of cutting edge 120. When insert 100 has been driven to an adequate depth into bore 134, screw 126 can be driven into inner peripheral surface 112 of insert 100 to an appropriate depth. As indicated by arrows in FIG. 9, screw 126 expands insert 100 against the tissues of bore 134. Distal end 104 is expanded radially outward into cancellous bone 132 so that cancellous bone 132 can provide anchoring strength in addition to the anchoring strength provided by cortical bone 130. With the particular screw 126 shown in FIG. 9, proximal end 106 is also expanded somewhat more than the middle portion of insert 100. In situations where it is not appropriate to distend the cortex 130, modified versions of screw 126 and/or insert 100 can be used so that proximal end 106 of insert 100 does not expand. Moreover, as described above, it is possible to provided different inner surface features to create different expansion patterns for inserts used in various applications.

Insert 100 can be used to increase anchoring strength of orthopedic screws in a variety of different applications, including fixation of broken bones, anchoring sutures, total joint replacements, acetabular cups, acetabular fixation, glenoid fixation, replacement hips, cervical plates, trauma plates, iliac procedures, anterior vertebral body fixation, pedicle fixation, facet fixation, dynamic stabilization devices, or any other suitable procedure. In some cases, the extra fixation strength provided by the insert can eliminate the need for longer bone screws, as in iliac wing surgery, for example. It is also possible to use insert 100 to repair failed fixations of traditional bone screws. Those skilled in the art will readily appreciate that insert 100 can be used in any other suitable application without departing from the spirit and scope of the invention. Those skilled in the art will further appreciate that the insert length, diameter, internal contours, and other configuration variables can differ from application to application.

In accordance with another aspect of the invention, a tool for affixing an orthopedic screw insert within bone tissue is provided. The tool includes a socket portion configured and adapted to engage a proximal section of an outer peripheral surface of an orthopedic screw insert. A driver extends distally from the socket portion and is configured and adapted to engage a section of an inner peripheral surface of the orthopedic screw insert distal from the socket portion.

Figures 10, 11:
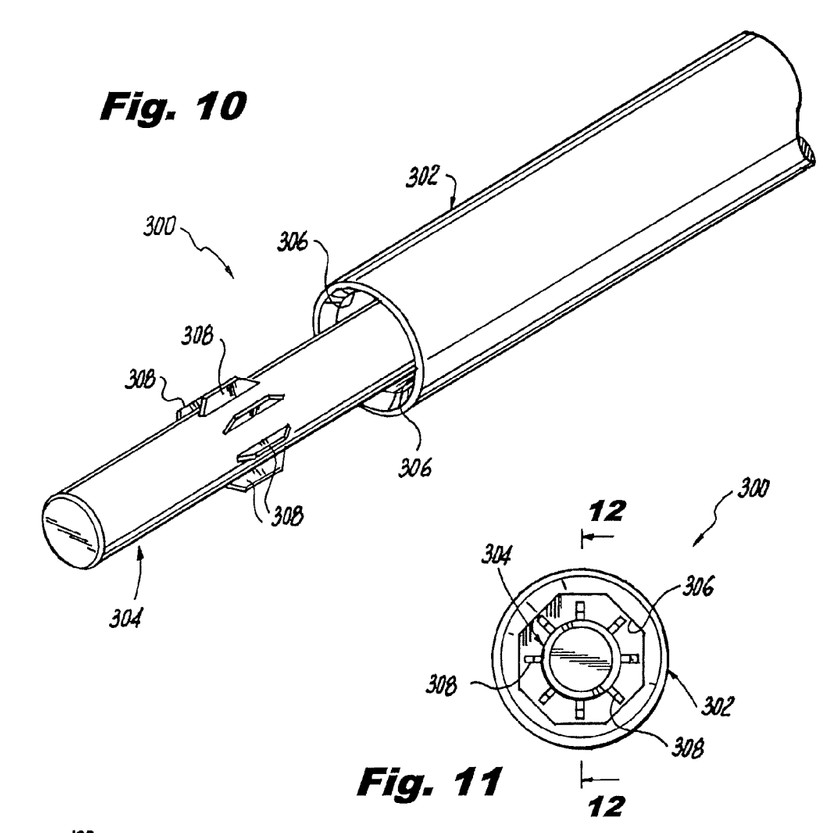
FIG. 10 is a perspective view of a portion of a tool for affixing an orthopedic screw insert within bone tissue in accordance with the invention, showing the socket portion and the driver extending therefrom.
FIG. 11 is distal end view of the tool of FIG. 10 in accordance with the invention, showing the polygonal section of the socket portion, as well as the fins of the driver.
Figure 12:
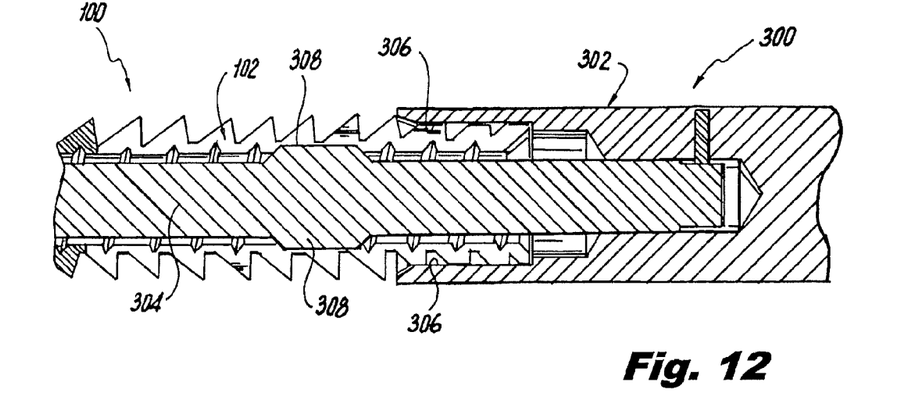
FIG. 12 is a cross-sectional side elevation view of a portion of the tool of FIG. 10 in accordance with the invention, showing the socket portion and driver engaging an orthopedic screw insert.

For purposes of illustration and not limitation, as embodied herein and as depicted in FIGS. 10-12, tool 300 includes a socket portion 302 with a faceted, polygonal portion 306 for engaging a polygonal portion of an orthopedic screw insert (e.g. insert 100). Polygonal portion 306 is hexagonal, however it is also contemplated that an octagonal or any other suitable configuration can be used as well. Socket portion 302 can be connected proximally to a manual drive or any other suitable driving means.

Driver 304 extends distally from within socket portion 302. Driver 304 includes radially extending fins 308 dimensioned to engage slots (e.g. slots 114a, 114b) of the insert. As shown in FIG. 11, driver 304 includes eight fins, one fin for engaging each slot of an insert with eight slots. The number and orientation of fins 304 can be varied depending on the number and orientation of slots in the insert. It is not necessary to have one fin for each slot, but at least one fin 304 can be included to provide driving engagement with a portion of the insert distal from socket portion 302.

FIG. 12 shows insert 100 engaged with tool 300. With the insert thus engaged, tool 300 can provide driving force at both proximal and distal portions of the insert. Driver 306 within the insert provides support for the flexible insert and prevents undesired flexing or distortion of the insert as it is driven into bone. Optional fins 308 provide even greater support by engaging slots 114a, 114b while driving the insert into bone. Thus tool 300 allows for the insert to be driven reliably, even when self-tapping of a bore is required.

Insert 100 can be utilized in conjunction with a variety of surgical procedures implementing orthopedic screws, as described above. To use insert 100, a suitable target site in a bone should be identified for locating a bone screw. A bore, e.g. bore 134, is drilled or otherwise formed in the bone at the target site. The bore can optionally be tapped for threading engagement with the insert. The insert is driven into the bore using a tool, e.g. tool 300 or any other suitable tool. A tool that provides support within the insert is advantageous as it reduces distortion of the insert while driving the insert into the bone. After removing the driving tool from the insert, an orthopedic screw can be mounted to the bone by driving the screw into the insert using any suitable driving means. With the orthopedic bone screw in place, the surgical procedure can be completed using the screw in a known manner.

While the apparatus and methods of the subject invention have been shown and described with reference to preferred embodiments, those skilled in the art will readily appreciate that various changes and/or modifications may be made thereto without departing from the spirit and scope of the subject invention as defined by the appended claims.

What is claimed is:

1. An insert for receiving a bone screw comprising:
   a) an elongate sleeve having opposed proximal and distal ends and a wall defined by an outer peripheral surface configured for engaging bone and an inner peripheral surface configured for receiving a bone screw extended therethrough; and
   b) at least one distal elongate slot formed in the wall of the sleeve extending from the distal end of the sleeve and at least one proximal elongate slot formed in the wall of the sleeve extending from the proximal end of the sleeve for promoting flexure of the insert, wherein the inner peripheral surface of the sleeve includes a threaded portion with internal threads configured for threaded engagement with threads of an orthopedic screw, wherein a distal portion of the inner peripheral surface is free of internal threads and has a uniform diameter that matches the minor diameter of the threaded portion to provide an expansion profile wherein the distal end of the sleeve is expanded more than a portion of the sleeve between the proximal and distal ends when an orthopedic screw is received in the sleeve for engaging a distal section of the outer peripheral surface with cancellous bone.

2. An insert as recited in claim 1, wherein the elongate sleeve has a middle region between the proximal and distal ends thereof, wherein the at least one distal slot extends from the distal end of the sleeve through the middle region toward the proximal end, and wherein the at least one proximal slot extends from the proximal end of the sleeve through the middle region toward the distal end, such that the proximal and distal slots overlap in the middle region of the sleeve.

3. An insert as recited in claim 2, wherein the middle region extends over at least 20% of the length of the sleeve.

4. An insert as recited in claim 3, wherein circumferentially alternating slots are distal slots in the middle region of the sleeve.

5. An insert as recited in claim 3, wherein the sleeve includes four distal slots and four proximal slots.

6. An insert as recited in claim 1, wherein the outer peripheral surface of the sleeve includes a sharpened helical cutting edge along at least a portion thereof, the sharpened edge being configured and adapted to increase fixation strength when the insert engages bone tissue through self-tapping.

7. An insert as recited in claim 1, further comprising a head portion at a proximal end of the sleeve, wherein the head portion is configured and adapted to engage a tool for driving the sleeve into a bone.

8. An insert as recited in claim 7, wherein the head portion includes a polygonal outer peripheral surface configured and adapted to engage a tool for driving the sleeve into a bone.

9. An insert as recited in claim 1, wherein the sleeve includes a biocompatible material selected from the group consisting of titanium alloys, plastics, composites and stainless steel.

10. An insert as recited in claim 1, further comprising a polymer coating disposed on at least a portion of the sleeve to provide resistance to turning of a bone screw when engaged within the insert.

11. An insert for receiving a bone screw comprising:
a) an elongate sleeve having opposed proximal and distal ends and a wall defined by an outer peripheral surface configured for engaging bone and an inner peripheral surface configured for receiving a bone screw extended therethrough; and
b) a plurality of elongate slots formed in the wall of the sleeve for promoting flexure of the insert and including:
i) at least one pair of diametrically opposed distal slots extending from the distal end of the sleeve; and
ii) at least one pair of diametrically opposed proximal slots extending from the proximal end of the sleeve, wherein the inner peripheral surface of the sleeve includes a threaded portion having internal threads configured for threaded engagement with threads of an orthopedic screw, wherein a distal portion of the inner peripheral surface is free of internal threads and has a uniform diameter that matches the minor diameter of the threaded portion to provide an expansion profile wherein the distal end of the sleeve is expanded more than a portion of the sleeve between the proximal and distal ends when a bone screw is received in the sleeve for engaging a distal section of the outer peripheral surface with cancellous bone.

12. An orthopedic system comprising:
a) an orthopedic screw;
b) an elongate sleeve engaged to the orthopedic screw and having opposed proximal and distal ends and a wall defined by an outer peripheral surface configured for engaging bone and an inner peripheral surface engaged with the orthopedic screw extended therethrough, the elongate sleeve including at least one distal elongate slot formed in the wall of the sleeve extending from the distal end of the sleeve and at least one proximal elongate slot formed in the wall of the sleeve extending from the proximal end of the sleeve for promoting flexure of the insert, wherein the inner peripheral surface of the sleeve includes internal threads engaged with threads of the orthopedic screw, wherein a distal portion of the inner peripheral surface is a thread-free portion pressed outward by the threads of the orthopedic screw to provide an expansion profile wherein the distal end of the sleeve is expanded more than a portion of the sleeve between the proximal and distal ends for engaging a distal section of the outer peripheral surface with cancellous bone.

13. An orthopedic system as recited in claim 12, wherein the orthopedic screw includes an enlarged proximal end engaged with the proximal end of the elongate sleeve, expanding the proximal end of the elongate sleeve more than the portion of the sleeve between the proximal and distal ends for engaging a proximal section of the outer peripheral surface of the elongate sleeve with cortical bone.

14. An insert as recited in claim 1, wherein the inner peripheral surface of the sleeve is contoured to provide an expansion profile wherein the proximal and distal ends of the sleeve are expanded more than a portion of the sleeve between the proximal and distal ends when a bone screw is received in the sleeve for engaging a proximal section of the outer peripheral surface with cortical bone and for engaging a distal section of the outer peripheral surface with cancellous bone.

15. An insert as recited in claim 11, wherein the inner peripheral surface of the sleeve is contoured to provide an expansion profile wherein the proximal and distal ends of the sleeve are expanded more than a portion of the sleeve between the proximal and distal ends when a bone screw is received in the sleeve for engaging a proximal section of the outer peripheral surface with cortical bone and for engaging a distal section of the outer peripheral surface with cancellous bone.

* * * * *